United States Patent
Ray et al.

(10) Patent No.: US 11,559,389 B2
(45) Date of Patent: Jan. 24, 2023

(54) BIOPRINTED LIVING TISSUE WITH THERAPY CAPABILITY

(71) Applicant: International Business Machines Corporation, Armonk, NY (US)

(72) Inventors: Abhidip Ray, Kolkata (IN); Olivi Roy Chowdhury, Kolkata (IN); Sarbajit K. Rakshit, Kolkata (IN)

(73) Assignee: International Business Machines Corporation, Armonk, NY (US)

( * ) Notice: Subject to any disclaimer, the term of this patent is extended or adjusted under 35 U.S.C. 154(b) by 372 days.

(21) Appl. No.: 16/866,786

(22) Filed: May 5, 2020

(65) Prior Publication Data
US 2021/0346147 A1    Nov. 11, 2021

(51) Int. Cl.
 *A61F 2/08*   (2006.01)
 *B33Y 80/00*  (2015.01)
 (Continued)

(52) U.S. Cl.
 CPC ............ *A61F 2/08* (2013.01); *B33Y 10/00* (2014.12); *B33Y 80/00* (2014.12); *G16H 20/30* (2018.01); *G16H 30/40* (2018.01); *G16H 40/67* (2018.01); *G16H 50/20* (2018.01); *H01L 41/042* (2013.01); *H01L 41/094* (2013.01); *H01L 41/317* (2013.01); *H01Q 1/273* (2013.01); *A61B 5/055* (2013.01); *A61B 5/4552* (2013.01); *A61F 2/482* (2021.08); *A61F 2002/0894* (2013.01); *A61F 2240/001* (2013.01); *A61F 2240/002* (2013.01); *A61F 2250/0001* (2013.01)

(58) Field of Classification Search
None
See application file for complete search history.

(56) References Cited

U.S. PATENT DOCUMENTS 9,566,428 B2    2/2017  Kawano et al.
9,610,457 B2 *  4/2017  Poon .................... A61H 1/008
(Continued)

FOREIGN PATENT DOCUMENTS

AU    2019204968 A1    8/2019
CA       2932021 A1    6/2015
(Continued)

OTHER PUBLICATIONS

Liu et al., "Progress in organ 3D bioprinting", Semantic Scholar, Published 2017, Review Article, 15 pages. https://www.semanticscholar.org/paper/Progress-in-organ-3-D-bioprinting-Liu-Liu/d046332dba158e8c46a9c76a4d696bfabafef048.
(Continued)

*Primary Examiner* — Jacqueline Woznicki
(74) *Attorney, Agent, or Firm* — Jeffrey M. Ingalls

(57) ABSTRACT

An artificial tongue is provided. The artificial tongue includes tongue tissue formed by a bioprinting process, an antenna embedded within the tongue tissue and configured to wirelessly receive power from an external device, a processor embedded within the tongue tissue and operatively coupled to the antenna, and a piezoelectric element embedded within the tongue tissue and operatively coupled to the processor. The piezoelectric element is configured to deform in response to an applied electric bias, and the processor is configured to cause the electric bias to be applied to the piezoelectric element based on the power received by the antenna.

20 Claims, 7 Drawing Sheets

(51) Int. Cl.
*G16H 40/67* (2018.01)
*G16H 30/40* (2018.01)
*H01L 41/04* (2006.01)
*H01L 41/09* (2006.01)
*H01L 41/317* (2013.01)
*H01Q 1/27* (2006.01)
*B33Y 10/00* (2015.01)
*G16H 20/30* (2018.01)
*G16H 50/20* (2018.01)
*A61B 5/00* (2006.01)
*A61B 5/055* (2006.01)
*A61F 2/48* (2006.01)

(56) References Cited

U.S. PATENT DOCUMENTS

| | | | | |
|---|---|---|---|---|
| 10,500,022 | B2* | 12/2019 | Yoon | A61C 7/14 |
| 2009/0085444 | A1* | 4/2009 | Alvarez Icaza Rivera | H02N 11/006 310/365 |
| 2009/0269329 | A1* | 10/2009 | Hyde | G16H 20/10 600/38 |
| 2011/0112601 | A1* | 5/2011 | Meadows | A61N 1/37247 607/42 |
| 2012/0123498 | A1* | 5/2012 | Gross | A61N 1/3601 607/42 |
| 2017/0014220 | A1* | 1/2017 | Gildener-Leapman | A61F 2/586 |
| 2017/0079262 | A1 | 3/2017 | Rowley et al. | |
| 2017/0119931 | A1 | 5/2017 | Arinzeh et al. | |
| 2019/0208363 | A1* | 7/2019 | Shapiro | A61B 5/0205 |
| 2019/0224956 | A1 | 7/2019 | Bostick et al. | |
| 2019/0255518 | A1 | 8/2019 | King et al. | |
| 2021/0001122 | A1* | 1/2021 | Toong | A61N 1/36034 |
| 2021/0162125 | A1* | 6/2021 | Altschul | A61B 5/14539 |
| 2021/0361406 | A1* | 11/2021 | Rakshit | G16H 40/63 |
| 2021/0369917 | A1* | 12/2021 | Christ | B33Y 80/00 |

FOREIGN PATENT DOCUMENTS

| | | | |
|---|---|---|---|
| CN | 104287875 A | 1/2015 | |
| CN | 104399119 A | 3/2015 | |
| CN | 104491927 A | 4/2015 | |
| WO | WO-2016201577 A1 * | 12/2016 | ........... B29C 64/106 |
| WO | 2019071018 A1 | 4/2019 | |

OTHER PUBLICATIONS

Katz et al., "Visual Feedback of Tongue Movement for Novel Speech Sound Learning", Front. Hum. Neurosci. 9:612. doi: 10.3389/fnhum, Nov. 19, 2015, 13 pages. https://www.frontiersin.org/articles/10.3389/fnhum.2015.00612/full.

Nowak, "3D Bioprinting Tissue and Organs", Prezi, 4 pages, Updated Jun. 2, 2017. https://prezi.com/vxzfmaxdenti/3d-bioprinting-tissue-and-organs/.

Mell et al., "The NIST Definition of Cloud Computing", Recommendations of the National Institute of Standards and Technology, Special Publication 800-145, U.S Department of Commerce, Sep. 2011, 7 pages.

Chowdhury, "Liver success holds promise of 3D organ printing", Special Report, Scientific Research, Financial Times, 6 pages, Mar. 2018. https://www.ft.com/content/67e3ab88-f56f-11e7-a4c9-bbdefa4f210b.

Little et al., "Printing the future: 3D bioprinters and their uses", Australian Academy of Science, printed Apr. 23, 2020, 14 pages. https://www.science.org.au/curious/people-medicine/bioprinting.

"3D Bioprinting of Living Tissues", WYSS Institute, Published Sep. 6, 2019, 8 pages. https://wyss.harvard.edu/technology/3d-bioprinting/.

Bhattacharya, "First human tongue transplant successful", NewScientist, The Daily Newsletter, Jul. 22, 2003, 4 pages. https://www.newscientist.com/article/dn3964-first-human-tongue-transplant-successful/.

"Piezoelectric Crystal Working and Applications", Electronics, Projects, Focus, EL-PRO-CUS, printed Apr. 23, 2020, 4 pages. https://www.elprocus.com/piezoelecliic-crystal-working-and-applications/.

International Search Report and Written Opinion, International Application No. PCT/CN2021/091416, dated Jul. 26, 2021, 9 pages.

* cited by examiner

BIOPRINTED LIVING TISSUE WITH THERAPY CAPABILITY

BACKGROUND

The present disclosure relates to biotechnology and to body tissue substitutes. In particular it relates to the fabrication of bioprinted body substitutes that include structural and software elements that facilitate integration and physical therapy of the transplanted body tissues.

In general, bioprinting refers to a process that takes cells from donor organs and builds up multiple layers of cells in calculated designs to form three-dimensional sections of tissue. One example of a body tissue substitute is a tongue. One of the challenges in tongue reconstruction and/or transplantation resides in its unique form and function. While most skeletal muscles of the human body move in a single plane, or at most two dimensions, the tongue is able to move in three dimensions. In addition, the tongue has the ability to volumetrically change the empty space of the oral cavity, thereby manipulating sound waves. While neurovascular connection or reconstruction of the tongue can be performed, replicating the tongue's complex movements can be challenging due to the tongue's reliance upon coordinated muscle activity between the tongue itself as well as the floor of mouth muscles, larynx, pharynx, upper palate and lips, etc. Therefore, complete functional rehabilitation of a transplanted tongue may be difficult, and it may depend on adequate restoration of the various sensory and motor functions.

SUMMARY

Embodiments of the present disclosure relate to a bioprinted artificial tongue. The artificial tongue includes tongue tissue formed by a bioprinting process, an antenna embedded within the tongue tissue and configured to wirelessly receive power from an external device, a processor embedded within the tongue tissue and operatively coupled to the antenna, and a piezoelectric element embedded within the tongue tissue and operatively coupled to the processor. The piezoelectric element is configured to deform in response to an applied electric bias, and the processor is configured to cause the electric bias to be applied to the piezoelectric element based on the power received by the antenna.

Other embodiments relate to method of manufacturing a bioprinted artificial tongue. The method includes bioprinting tongue tissue, forming an antenna within the tongue tissue, the antenna configured to wirelessly receive power from an external device, forming a processor within the tongue tissue, the processing being operatively coupled to the antenna, and forming a piezoelectric element within the tongue tissue. The piezoelectric element is operatively coupled to the processor and is configured to deform in response to an applied electric bias. The processor is configured to cause the electric bias to be applied to the piezoelectric element based on the power received by the antenna.

The above summary is not intended to describe each illustrated embodiment or every implementation of the present disclosure.

BRIEF DESCRIPTION OF THE DRAWINGS

The drawings included in the present application are incorporated into, and form part of, the specification. They illustrate embodiments of the present disclosure and, along with the description, explain the principles of the disclosure. The drawings are only illustrative of certain embodiments and do not limit the disclosure.

Figure 1A:
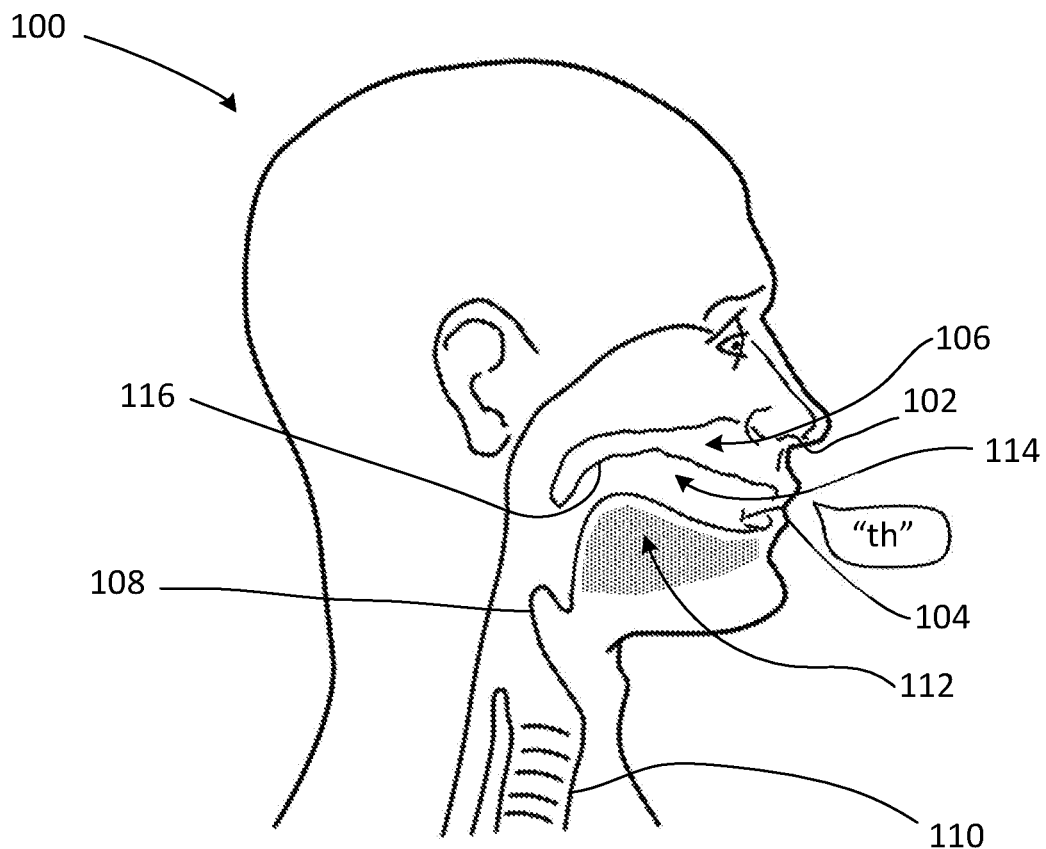
FIG. 1A is a side view of bioprinted tongue in a first position.

It should be appreciated that elements in the figures are illustrated for simplicity and clarity. Well-understood elements that may be useful or necessary in a commercially feasible embodiment may not be shown for the sake of simplicity and to aid in the understanding of the illustrated embodiments.

DETAILED DESCRIPTION

The present disclosure relates to bioprinted tissues, and to systems for controlling the movement and position of the bioprinted tissues. In particular, embodiments of the present disclosure relate to a bioprinted tongue that can be transplanted into a patient, and then programmatically controlled during subsequent speech therapy to create controlled movements of tongue muscles. The controlled movements of the tongue may enable more efficient and effective therapy, and may speed the recovery process for a patient. In certain embodiments, the bioprinted tongue is not simply used for the initial therapy but may facilitate proper movement of the tongue muscles for an entire life cycle of the bioprinted transplanted tongue.

In general, bioprinting is a process that takes cells from donor organs and turns these cells into a printable bio-ink. Layers of cells are laid down in calculated designs to build up small sections of tissue. For example, bioprinting can be utilized to create artificial bone, skin, blood vessels, tongue tissue, and a variety of different internal organs, etc. In one example method of bioprinting, the cells are taken from a person and cultured so that they can multiply. Then, the cultured cells are loaded into a specialized bioprinter. The cells are then layered, for example, using a hydrogel as a supporting structure. Finally, as several layers of cells are printed into a three-dimensional (3D) structure, they grow into mature tissue and are able to be used for medical purposes. It should be appreciated that this is merely one example method of utilizing bioprinting to form tissues (e.g., a tongue), and any suitable bioprinting method may be used in the context of the presently disclosed embodiments. That is, the bioprinting approach can be modified in any suitable manner to create various 3D tissues for regenerative medicine, drug testing endeavors, as well as body part transplantation. With a bioprinted tongue, it may be desirable to ensure that the tongue moves properly while speaking, that the tongue touches different portions of the mouth, and accordingly different types of sound are generated. If the tongue does not move properly, then the user will not be able to speak properly. Thus, it may be desirable to ensure proper movement of the tongue inside the mouth.

In certain embodiments, piezoelectric devices (e.g., piezoelectric actuator strips) may be utilized to control the movement or position of the bioprinted tongue. In general, a piezoelectric actuator converts an electrical signal (or electrical bias) into a precisely controlled physical displacement (i.e., a stroke). Elementary piezoelectric materials change dimensions when an electric current and/or voltage is applied. As a corollary, if a force is applied to the piezoelectric device, an electric current and/or voltage may be generated. Piezoelectric actuators give off relatively low amounts of heat and consume small amounts of power when operating in an energized state, and thus may be suitable for biological transplantation systems. One example type of piezoelectric actuator is known as a stripe actuator (also called a bending actuator), and it is designed to produce a relatively large mechanical deflection in response to an electrical signal. This deflection offers a large stroke and a very limited blocking force when compared to a stack actuator (i.e., low stroke and high blocking force). In a stripe actuator, two thin layers of piezoelectric ceramic are bonded together, usually with the direction of polarization coinciding, and are electrically connected in parallel. When electrical input is applied, one ceramic layer expands and the other contracts causing the actuator to flex. In the present embodiments discussed below, one or more piezoelectric devices may be embedded into (or printed into) a bioprinted tongue, and the flexing of the piezoelectric devices can be coordinated to precisely change the position of specific portions of the tongue.

In the present embodiments, neural networks and other deep learning systems may be utilized to aid in speech therapy by intelligently controlling the deformation and flexure of the various piezoelectric devices implanted in the bioprinted tongue to move different portions of the muscle into desired positions. An Artificial Neural Network (ANN) (also referred to more generally as a neural network) is a computing system made up of a number of simple, highly interconnected processing elements (nodes), which process information by their dynamic state response to external inputs. ANNs are processing devices (algorithms and/or hardware) that are loosely modeled after the neuronal structure of the mammalian cerebral cortex, but on much smaller scales. Such systems progressively and autonomously learn tasks by means of examples, and they have successfully been applied to, for example, speech recognition, text processing and computer vision. A large ANN might have hundreds or thousands of processor units, whereas a mammalian brain has billions of neurons with a corresponding increase in magnitude of their overall interaction and emergent behavior.

Many types of neural networks are known, starting with feedforward neural networks, such as multilayer perceptrons, deep learning neural networks (DNNs) and convolutional neural networks. A feedforward neural network is an artificial neural network (ANN) where connections between the units do not form a cycle. A deep learning neural network is an artificial neural network with multiple hidden layers of units between the input and output layers. Similar to shallow ANNs, DNNs can model complex non-linear relationships. DNN architectures, e.g., for object detection and parsing, generate compositional models where the object is expressed as a layered composition of image primitives. The extra layers enable composition of features from lower layers, giving the potential of modeling complex data with fewer units than a similarly performing shallow network. DNNs are typically designed as feedforward networks.

In certain embodiments, neural networks and other deep learning systems may be utilized to generate speech therapy models based on, for example, capturing tongue movement patterns from MRI image analysis, historically spoken content from one or more users, and sounds corresponding to different tongue movement patterns. These training models may be used to aid in speech therapy by intelligently controlling the deformation and flexure of the various piezoelectric devices implanted in the bioprinted tongue to move different portions of the tongue muscle into desired positions.

Various embodiments of the present disclosure are described herein with reference to the related drawings. The flowcharts and cross-sectional diagrams in the Figures illustrate these systems and methods according to various embodiments. In some alternative implementations, the steps in the flowcharts may occur in a different order that that which is noted in the Figures. Alternative embodiments can be devised without departing from the scope of the present disclosure. It is noted that various connections and positional relationships (e.g., over, below, adjacent, etc.) are set forth between elements in the following description and in the drawings. These connections and/or positional relationships, unless specified otherwise, can be direct or indirect, and the present disclosure is not intended to be limiting in this respect. Accordingly, a coupling of entities can refer to either a direct or an indirect coupling, and a positional relationship between entities can be a direct or indirect positional relationship. As an example of an indirect positional relationship, references in the present description to forming layer "A" over layer "B" include situations in which one or more intermediate layers (e.g., layer "C") is between layer "A" and layer "B" as long as the relevant characteristics and functionalities of layer "A" and layer "B" are not substantially changed by the intermediate layer(s).

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

For purposes of the description hereinafter, the terms "upper," "lower," "right," "left," "vertical," "horizontal," "top," "bottom," and derivatives thereof shall relate to the described structures and methods, as oriented in the drawing figures. The terms "overlying," "atop," "on top," "positioned on" or "positioned atop" mean that a first element, such as a first structure, is present on a second element, such as a second structure, wherein intervening elements can be present between the first element and the second element. The term "direct contact" means that a first element, such as a first structure, and a second element, such as a second structure, are connected without any intermediary structures at the interface of the two elements.

Figure 1B:
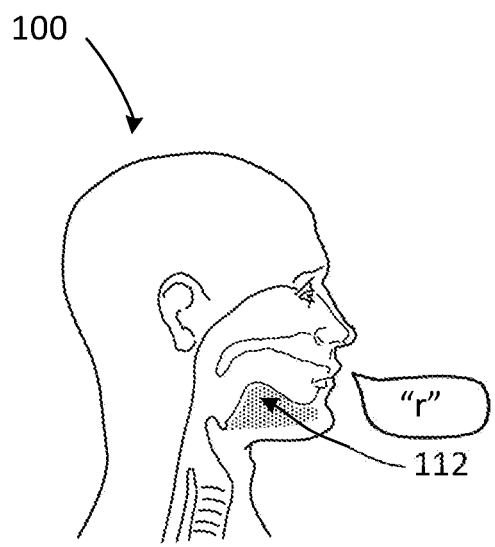
FIG. 1B is a side view of the bioprinted tongue of FIG. 1A in a second position.
Figure 1C:
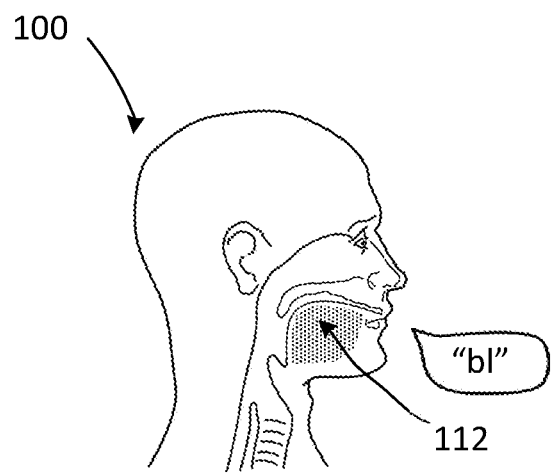
FIG. 1C is a side view of the bioprinted tongue of FIG. 1A in a third position.

Referring now to the drawings in which like numerals represent the same or similar elements and initially to FIG. 1, several examples of tongue positions are shown, where each different tongue position relates to a different sound. A human 100 is shown with various body parts that are related to speech. In particular, FIG. 1A illustrates the palate 106 of the mouth, the roof 116 of the mouth, the oral cavity 114, the lips 104, the nose 102, the epiglottis 108, the larynx 110 and the tongue 112. As shown in FIG. 1A, the tongue 112 is located in a first position to form, for example, a "th" sound. In FIG. 1B, the tongue 112 is located in a second position to form, for example, an "r" sound. In FIG. 1C, the tongue 112 is located in a third position to form a "bl" sound. It should be appreciated that the examples shown in FIGS. 1A-1C are merely presented to illustrate that the tongue can be located in a variety of different positions (i.e., relative to the lips 104, the roof 116 of the mouth, and within the oral cavity 114, etc.) to form a myriad of different sounds. In certain of the present embodiments, the bioprinted tongue can be moved into these different positions with the use of (or the aid of) embedded piezoelectric strips, one or more processors, a power source, and a knowledge corpus that is based, for example, on machine learning and/or a deep learning neural network. In general, the knowledge corpus includes information regarding relationships between tongue positions and sound, and the processor causes electricity to be applied to the piezoelectric strips in accordance with information contained in this knowledge corpus. The electricity (i.e., current or voltage) applied to the piezoelectric strips causes the strips to bend or deform, which in turn causes the bioprinted tongue to distort in a particular manner corresponding to the desired tongue position associated with a particular sound.

Figure 2:
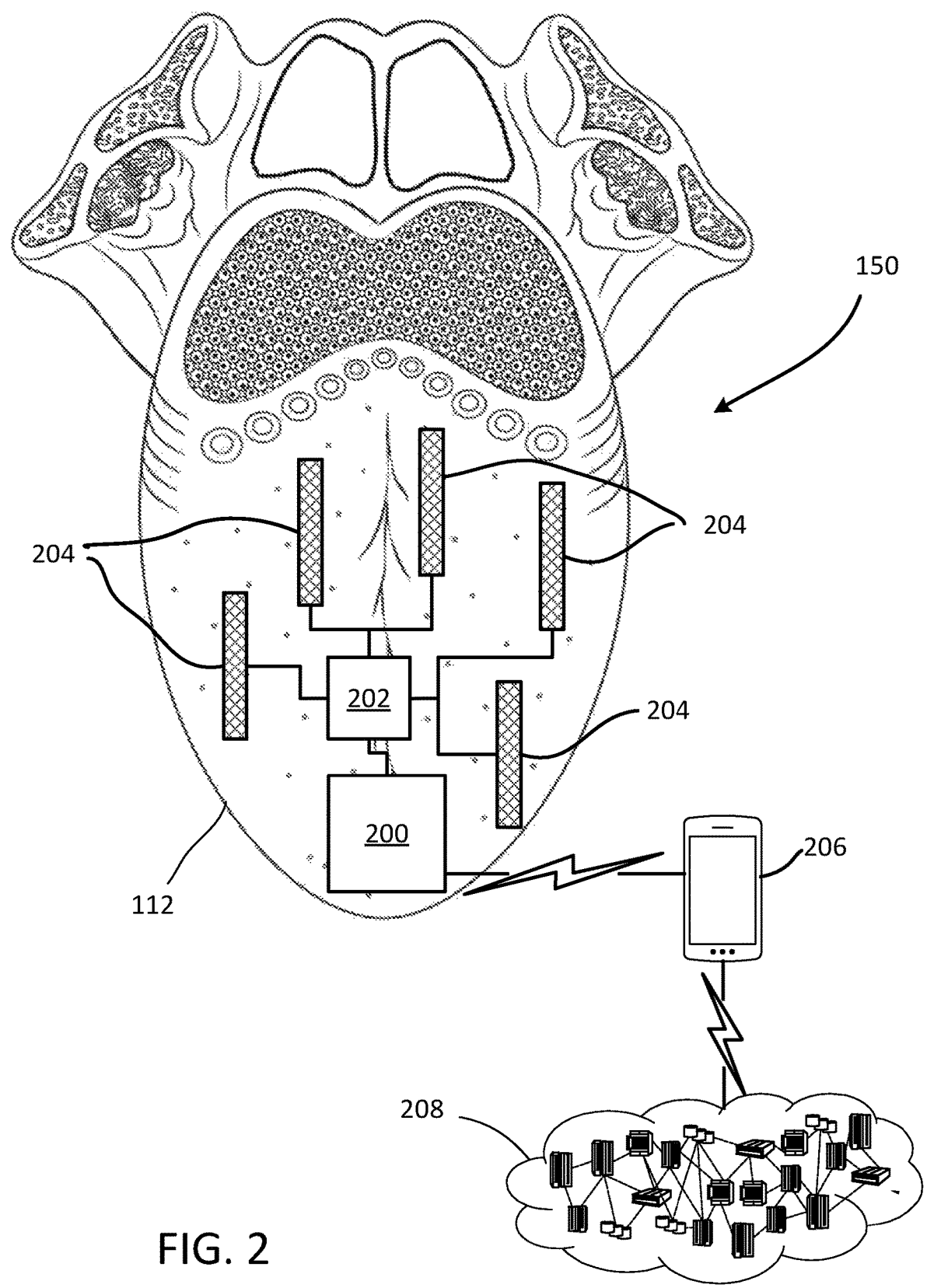
FIG. 2 is a schematic diagram of a bioprinted tongue system, according to embodiments.

Referring now to FIG. 2, an example of a bioprinted tongue system 150 is shown. As shown in FIG. 2, the bioprinted tongue system 150 includes a bioprinted tongue 112 and an external mobile device 206 connected to a network 208. As discussed in detail below, the external mobile device 206 may be a cellular phone, and this is merely one example of a mobile device that is able to communicate with and transfer power to the bioprinted tongue 112. It should be appreciated that any other suitable type of mobile device may be used.

In certain embodiments, the bioprinted tongue 112 includes a processor 202, an antenna 200 and a plurality of piezoelectric strips 204. In certain embodiments, the processor 202 (or printed integrated circuit) is printed (or formed) inside the bioprinted tongue 112 and includes a unique identifier. In these embodiments the bioprinted tongue 112 is controlled by an external mobile device 206 according to this unique identifier.

In other embodiments, one or more of the processor 202, the antenna 200 and the plurality of piezoelectric strips 204 may be surgically implanted in a patient's actual tongue (i.e., not a bioprinted tongue) to aid in speech therapy. In these embodiments, these components could be separately manufactured, and then inserted into the tongue.

In certain embodiments, the antenna 200 is configured to wirelessly receive power from a wireless power source and distribute the energy from the antenna 200 to the processor 202 and/or the piezoelectric strips 204. The antenna 200 may receive a power according to one or more of a variety of different wireless charging techniques. One technique utilizes a charging pad that uses tightly-coupled electromagnetic inductive or non-radiative charging. Another technique utilizes charging bowls or through-surface type chargers that use loosely-coupled or radiative electromagnetic resonant charging that can transmit a charge a few centimeters. Both tightly coupled inductive and loosely-coupled resonant charging techniques operate on the same principle of physics: a time-varying magnetic field that induces a current in a closed loop of wire (e.g., the antenna 200). Another technique is to use uncoupled radio frequency (RF) wireless charging that allows a trickle charging capability at distances of many feet. The radio frequency wireless charging may be particularly effective in the present embodiments, where the wireless power source can be located at greater distances from the bioprinted tongue 112 so as to not interfere with the speech functions or the movement of the tongue.

In certain embodiments, the antenna 200 is also configured to receive information or other suitable speech therapy instructions. This information can be processed by the processor 202 to generate controlled electrical signals to be sent to the various piezoelectric strips 204. This information may be received directly from an external mobile device 206 (or more generally an external device), such as the user's cellular phone. In other examples, the information may be received indirectly from a network 208. In these examples, information is transferred wirelessly from the network 208 to the external mobile device 206, and then from the external mobile device 206 to the antenna 200 of the bioprinted tongue 112. As mentioned above, the example of the cellular phone as an external mobile device 206 is only one example of a device that can wireless connect the bioprinted tongue 112 to the network 208, and any other suitable wireless device may be used.

In certain embodiments, the wireless power source is the battery of the external mobile device 206 (e.g., a smartphone or personal digital assistant (PDA), etc.). In these embodiments, the battery of the external mobile device 206 can be used to power the device itself, and also wirelessly transmit a portion of its power to the bioprinted tongue 112. In examples where the external mobile device 206 uses an uncoupled radio frequency (RF) wireless charging technique, the user may be able to position the phone several feet away from the bioprinted tongue 112 (e.g., in their pocket, on a nearby desk, or plugged in to a nearby charging station). Also, in certain embodiments, the external mobile device 206 may have installed thereon one or more physical therapy or speech training software applications. In these embodiments, the user may view the display screen of the external mobile device 206 and follow any instructions provided by the application for speech therapy, while simultaneously receiving power from the battery of the external mobile device 206 to run the various components of the bioprinted tongue 112. Although the example of a battery of a cellular phone (i.e., the external mobile device 206) is described above, it should be appreciated that the power source may be any suitable device capable of transmitting sufficient energy to the antenna 200 and thereby power the processor 202, the piezoelectric strips 204, and any other peripheral power consuming components of the bioprinted tongue 112.

As shown in FIG. 2, in certain embodiments, the bioprinted tongue 112 includes a plurality of piezoelectric strips 204 that are connected to the processor 202. In the embodiments shown in FIG. 2, the antenna 200 wirelessly receives the power from the external mobile device 206 and distributes it to the processor 202, which in turn distributes a portion of that power to the piezoelectric strips 204. However, in other embodiments, the power is distributed directly from the antenna 200 to the piezoelectric strips 204 (i.e., without the processor 202 as an intermediate element).

In FIG. 2, the piezoelectric strips 204 are shown to distributed at various locations of the tongue 112. However, it should be appreciated that this is merely for the sake of illustration, and the piezoelectric strips 204 may be distributed in any suitable manner according to the musculature of a given tongue 112, and according to the desired deflections required to achieve certain sounds. Also, the piezoelectric strips 204 (which are generally elongated rectangular shapes) are shown to extend in a front-to-back direction of the tongue 112. However, they may be oriented in any suitable direction, and certain of the piezoelectric strips 204 may be oriented in a different direction than the others (i.e., some may extend in a diagonal direction relative to a front-to-back direction of the tongue 112).

Moreover, the piezoelectric strips 204 may be positioned at different depths within the thickness of the tongue 112. As discussed above, the 3D bioprinting process may involve printing the cells of the tongue 112 in a layer-by-layer configuration. In this manner, the piezoelectric strips 204 may be formed (or 3D printed) at an intermediate location in the thickness of the tongue 112 (i.e., in the middle stages of manufacturing the 3D product). In this regard, certain of the piezoelectric strips 204 may be located at a different thickness position of the tongue 112 relative to other of the piezoelectric strips 204. In addition, in certain examples, multiple piezoelectric strips 204 can be stacked over one another in plan view (i.e., a top down view) in order to increase the flexing strength of the stack of strips. In other words, for example, assuming that it takes more energy to flex the central portion of the tongue 112 (i.e., where there may be a greater thickness of tissue) than the side portions of the tongue 112, multiple piezoelectric strips 204 can be stacked in this central portion to increase the overall flexing strength in that region. In certain embodiments, while performing layer-by-layer printing of tongue 112, the piezoelectric strips 204 will also be printed in layers.

As shown in FIG. 2, the bioprinted tongue 112 also includes a processor 202 (e.g., an integrated circuit chip). The processor 202 is operatively coupled to each of the piezoelectric strips 204 and is configured to individually control the application of current/voltage to the piezoelectric strips 204. This allows individual control of whether a particular piezoelectric strip 204 receives current/voltage, and how much current/voltage is received. Thus, for a particular sound (e.g., the "th" sound shown in FIG. 1A) and associated tongue position, only some of the piezoelectric strips 204 may be activated, and some of the piezoelectric strips 204 may receive more/less current/voltage than others. Likewise, for a different particular sound (e.g., the "r" sound shown in FIG. 1B) and associated tongue position, a different combination of piezoelectric strips 204 may be activated relative to the "th" sound, and different of the piezoelectric strips 204 may receive more/less current/voltage than the others.

As indicated above, in certain embodiments, the processor receives instructions regarding bioprinted tongue 112 movements from an external source (such as the network 208 or the external mobile device 206). These instructions for tongue movements may be in accordance with a speech/physical therapy program designed by a medical professional, they may be in accordance with text (e.g., a book or a magazine), or any other suitable source. These instructions can then be interpreted by the processor 202 and relayed to the piezoelectric strips 204 to cause movement of the tongue 112. In certain embodiments, the control of the piezoelectric strips 204 can be timed to be in synchronization with other instructions provided to a user on a display device (e.g., a display screen of the external mobile device 206). In this regard, the display device may display a word or a sentence to a user and instruct the user to begin speaking the word at a given time. As the user attempts to speak this word by moving the bioprinted tongue 112, this effort of the user may be augmented (or assisted) with the controlled deformation of the piezoelectric strips 204. In other embodiments, during speech therapy, the bioprinted tongue system 150 will create a visualization of the tongue muscle movement pattern on the display screen of the external mobile device 206, and the piezoelectric strips 204 will produce additional force on the bioprinted tongue 112 muscle. In this manner, the user can understand how they should talk by viewing this information on the display screen.

As discussed above with regard to the functioning of piezoelectric devices in general, if a force is applied to the piezoelectric strip 204, an electric current and/or voltage may be generated. As such, if a user undergoing speech therapy attempts to move the tongue 112 alone (i.e., without the assistance of the piezoelectric strips 204) stress/strain is applied to the piezoelectric strips 204, thereby generating a certain amount of electricity. In certain embodiments, the bioprinted tongue system 150 includes sensors (not shown) that can measure the user generated electrical current in each of the piezoelectric strips 204, and then transmit this information to the processor 202. Thus, in certain embodiments, the processor 202 is capable of processing a measurement of these user generated electrical currents, which can allow insight into the unassisted strength of the user's bioprinted tongue 112. Therefore, in certain examples, the progress of the user's recovery or therapy can be tracked over time by storing these current measurements in a memory device (e.g., the memory device 302 of FIG. 3, or the RAM 510 or ROM 508 of FIG. 5). By monitoring the progress of the user in this manner, speech therapy can potentially be modified based on an individual's progress. For example, if a user is struggling with a particular sound (e.g., "th") or tongue position as evidenced by the historical user current measurements, the speech therapy program may be modified to produce more/less deflection assistance with regard to certain piezoelectric strips 204. In other words, if there is an indication that a user is struggling with unassisted movement of the left side of the tongue, the speech therapy program can be modified to increase the assistance with regard to the piezoelectric strips 204 located on that side of the tongue 112.

Figure 3:
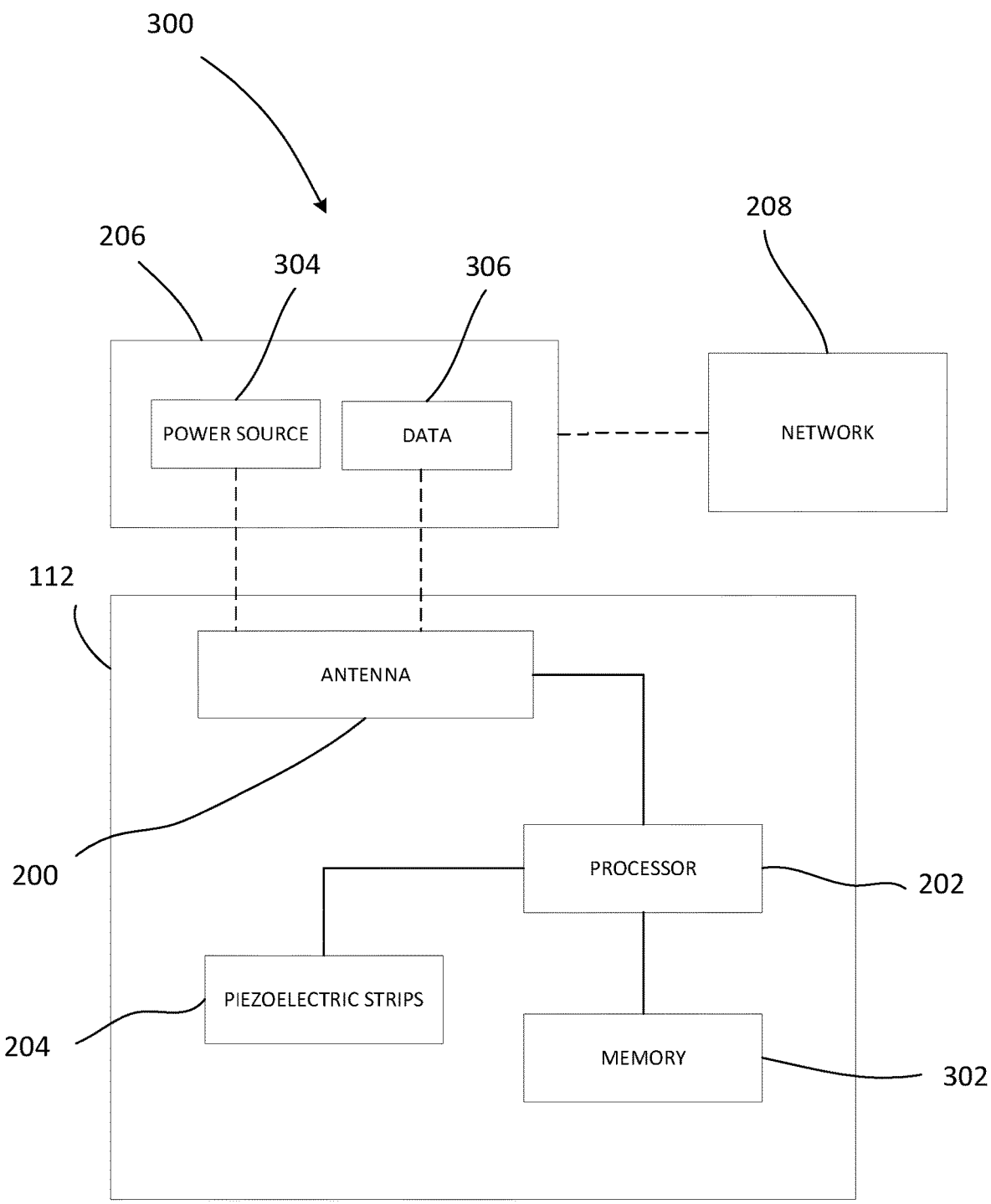
FIG. 3 is a block diagram of a bioprinted tongue system, according to embodiments.

Referring now to FIG. 3, a schematic view of bioprinted tongue system 300 is shown. The system 300 includes a bioprinted tongue 112, an external mobile device 206 operatively coupled to the bioprinted tongue 112, and a network 208 operatively coupled to the mobile device 206. The external mobile device 206 includes a power source 304 and is configured to transmit power and data 306 through an antenna (not shown) of the external mobile device 206. The bioprinted tongue 112 includes an antenna 200 configured to receive the power and data 306 transmitted by the external mobile device 206. The bioprinted tongue 112 also includes a processor 202 operatively coupled to the antenna 200. In certain embodiments, the bioprinted tongue 112 also includes a memory device 302 that is operatively coupled to the processor 202. Also, the bioprinted tongue 112 includes a plurality of piezoelectric strips 204 that are electrically connected to the processor 202. The processor 202 is configured to cause electrical signals to be sent to the piezoelectric strips 204, thereby causing a deflection or flexing thereof.

It should be appreciated that in certain embodiments, the bioprinted tongue system 300 also includes a power storage device (e.g., a battery or a capacitor—not shown). In these embodiments, the power that is received through the antenna may be stored in the battery for use by the processor and the piezoelectric strips (or any other component of the bioprinted tongue system 300). In this case, even if the external mobile device 206 is not actively transferring power to the bioprinted tongue system 300, the system may still be able to operate with the energy contained within the power storage device.

It should be appreciated that in the embodiments where the bioprinted tongue 112 includes the memory device 302, the memory device 302 may include instructions or other data that (e.g., information that is associated with certain sounds or tongue positions, and related instructions to move certain of the piezoelectric strips 204 into certain positions associated with these sounds) may enable movement of the tongue without the assistance of the external mobile device 206. Therefore, if the external mobile device 206 is not working, is out of power, not near to the tongue, or otherwise not transmitting data/power, the bioprinted tongue 112 may still be able to operate for a period of time based on at least one of the memory device 302 and the power storage device (not shown).

Figure 4:
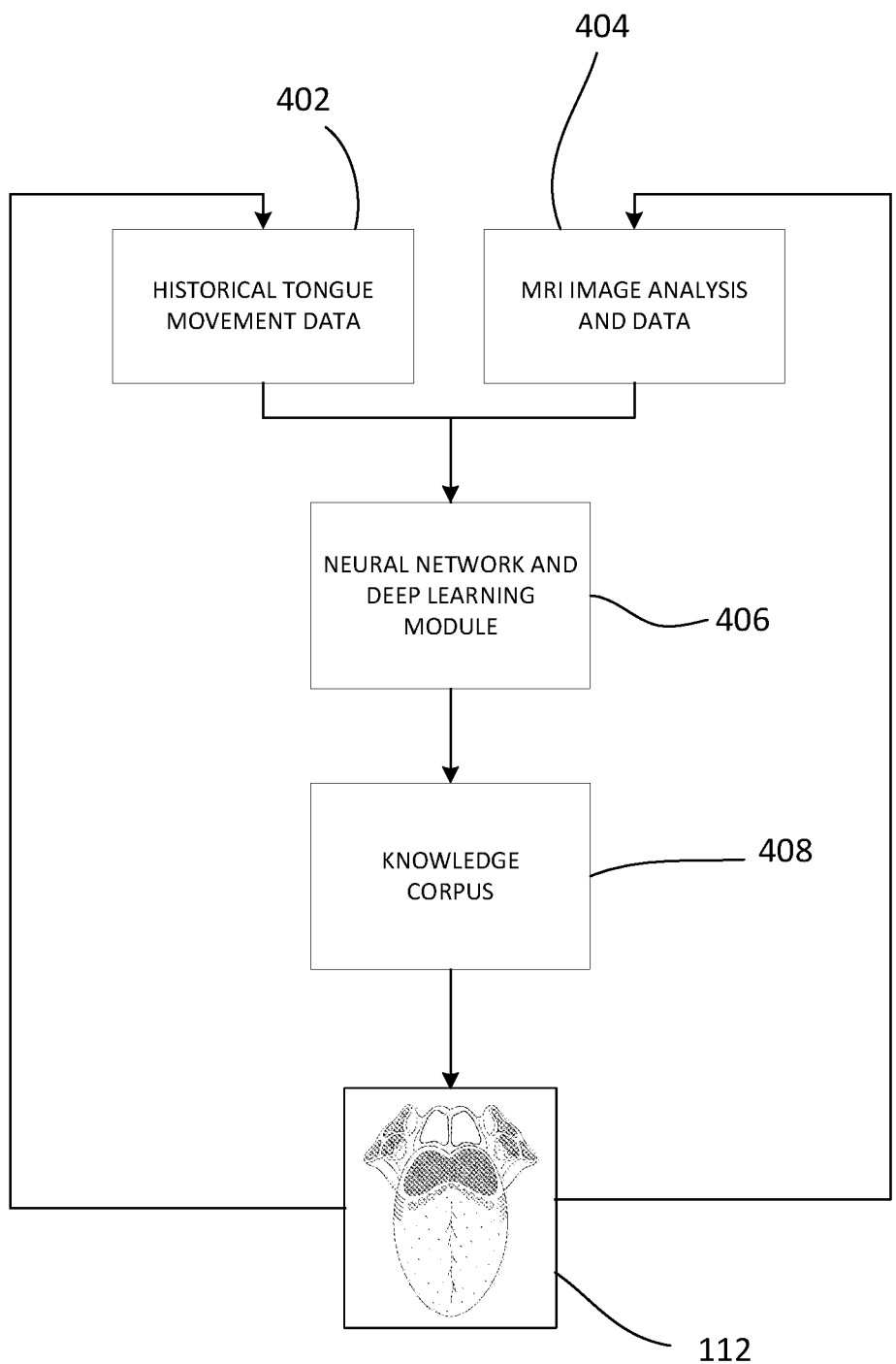
FIG. 4 is a block diagram of a method of training a knowledge corpus for a bioprinted tongue system, according to embodiments.

Referring now to FIG. 4, an example embodiment is shown utilizing a neural network and deep learning module 406 to create a knowledge corpus 408 to aid in performing speech therapy. In this embodiment, historical tongue movement data 402 and MRI image analysis and data 404 is fed into the neural network and deep learning module 406 to create the knowledge corpus 408. The historical tongue movement data 402 can be based on an individual user, or a plurality of different users. The knowledge corpus 408 is then used to perform effective therapy on a user's bioprinted tongue 112. In turn, the speech therapy performed on the bioprinted tongue 112 can be used to gather addition MRI and movement data that can used to further refine the knowledge corpus 408. In certain embodiments, the system captures tongue movement patterns from MRI image analysis, as well as historical spoken content from a variety of different users and adds this to the knowledge corpus 408. Sounds associated with tongue movement patterns are also gathered an added to the knowledge corpus 408. Once the knowledge corpus 408 is created, the system will be able to simulate tongue muscle movement patterns, and accordingly be able to identify how the bioprinted tongue 112 muscle should be moving. Based on the tongue muscle movement patterns, the system will also be able to calculate how much force is required for different bioprinted tongue 112 movements.

In certain embodiments, machine learning is performed with respect to the bioprinted tongue 112 movement patterns inside the mouth, and accordingly, sound generation from the mouth and the bioprinted tongue 112 touching in different portions of the mouth are identified. In certain embodiments, based on the movement patterns of the bioprinted tongue 112 inside the mouth, the system may identify which portion of the bioprinted tongue 112 muscle needs additional force. In certain embodiments, based on bioprinted tongue 112 muscle movement patterns, the system identifies how much force is required to move the bioprinted tongue 112 muscle, and this can be based on the unit weight of the tissue and/or a movement distance required to move that portion of the bioprinted tongue 112 to a particular position. In certain embodiments, the system also identifies the sequence of bioprinted tongue 112 muscle movements needed to perform a particle movement of the bioprinted tongue 112 inside the mouth. In certain embodiments, the system identifies how much power is required for a particular movement of the bioprinted tongue 112 muscle.

In certain embodiments, the system is configured to create a 3D simulation of the bioprinted tongue 112 for manufacturing purposes, and this 3D simulation considers each of the required bioprinted tongue 112 movements and movement patterns. The system also simulates different spoken content and sound generation techniques. The simulation engine generates a model of how the piezoelectric strips are to be printed inside the tongue muscle, so that the piezoelectric strips can also produce a similar muscle movement and create the required force in the bioprinted tongue 112. Based on the required force to be produced externally, the system will simulate how many piezoelectric strips are to be printed, and the position of the piezoelectric strips inside the bioprinted tongue 112 muscle. The simulation engine identifies the position of the piezoelectric strips inside the bioprinted tongue 112 muscle so that it can produce the required muscle movements. The knowledge corpus 408 will also capture the muscle movement sequences when any bioprinted tongue 112 moves as a user speaks. In certain embodiments, the sequence of bioprinted tongue 112 muscle movements is stored in a processor 202, or another memory device. In certain embodiments, the processor 202 (or printed circuit) controls the movement of the individual piezoelectric strips 204 printed in different positions of the bioprinted tongue 112. Each of the piezoelectric strips 204 are identified based on the position of the bioprinted tongue 112, and accordingly, the processor 202 will control each and every piezoelectric strip 204 individually When the simulation of the bioprinted tongue 112 along with piezoelectric strips 204 and processor 202 is created, then the proposed system initiates 3D tongue printing according to this simulation.

Figure 5:
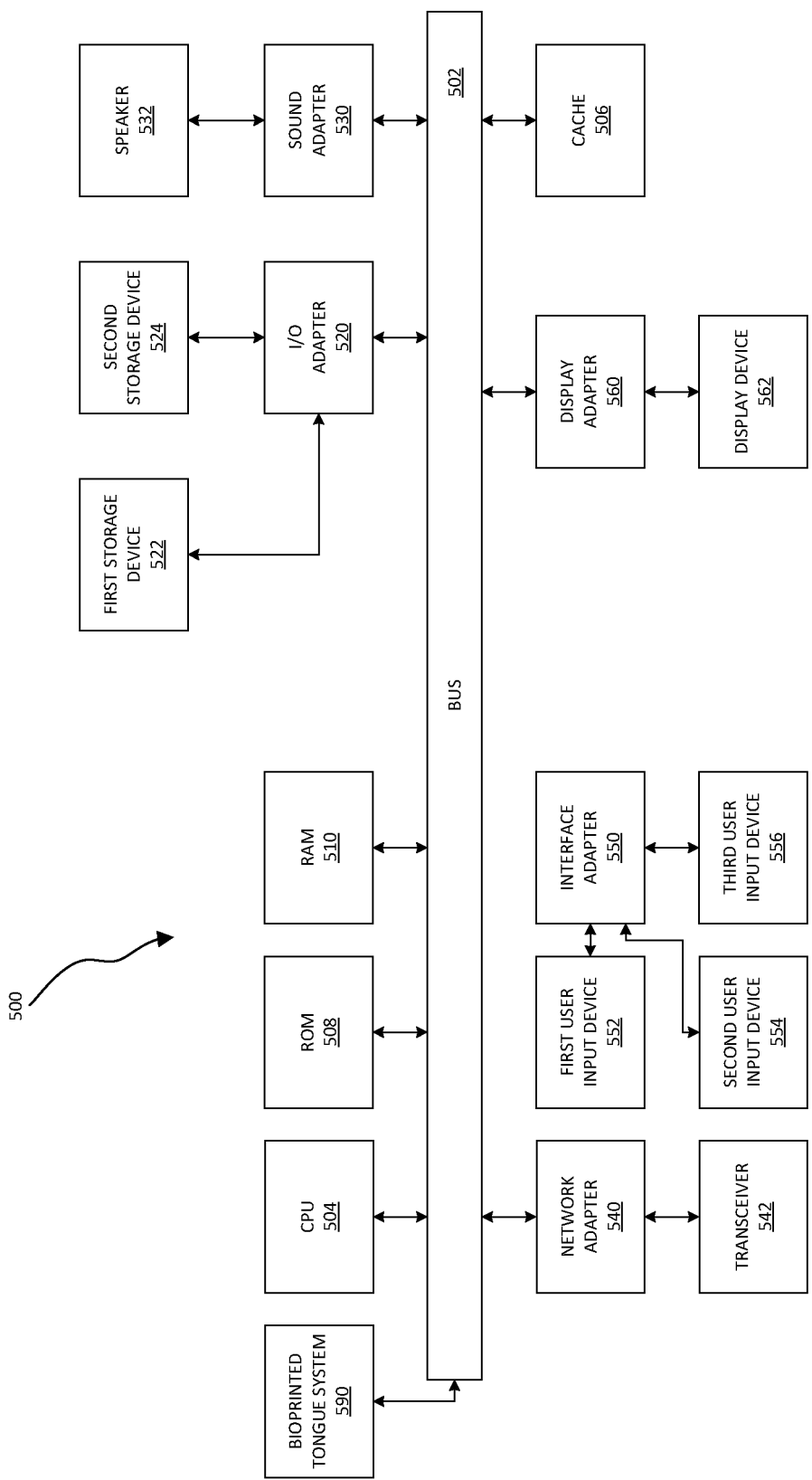
FIG. 5 depicts a block diagram of a processing system, according to embodiments.

Referring now to FIG. 5, an exemplary processing system 500 to which the present embodiments may be applied is shown in accordance with one embodiment. The processing system 500 includes at least one processor (CPU) 504 operatively coupled to other components via a system bus 502. A cache 506, a Read Only Memory (ROM) 508, a Random-Access Memory (RAM) 510, an input/output (I/O) adapter 520, a sound adapter 530, a network adapter 540, a user interface adapter 550, and a display adapter 560, are operatively coupled to the system bus 502.

A first storage device 522 and a second storage device 524 are operatively coupled to system bus 502 by the I/O adapter 520. The storage devices 522 and 524 may be any of a disk storage device (e.g., a magnetic or optical disk storage device), a solid-state magnetic device, and so forth. The storage devices 522 and 524 may be the same type of storage device or different types of storage devices.

A speaker 532 is operatively coupled to system bus 502 by the sound adapter 530. A transceiver 542 is operatively coupled to system bus 502 by network adapter 540. A display device 562 is operatively coupled to system bus 502 by display adapter 560.

A first user input device 552, a second user input device 554, and a third user input device 556 are operatively coupled to system bus 502 by user interface adapter 550. The user input devices 552, 554, and 556 may be any of a keyboard, a mouse, a keypad, an image capture device, a motion sensing device, a microphone, a device incorporating the functionality of at least two of the preceding devices, or any other suitable types of input devices. The user input devices 552, 554, and 556 may be the same type of user input device or different types of user input devices. The user input devices 552, 554, and 556 are used to input and output information to and from system 500. In certain embodiments, a graphics processing unit (GPU) 570 is operatively coupled to system bus 502. In these embodiments, the GPU performs training and inference on the MRI images of the bioprinted tongue system 590 with a deep learning object detection model.

The processing system 500 may also include other elements (not shown), as readily contemplated by one of skill in the art, as well as omit certain elements. For example, various other input devices and/or output devices may be included in processing system 500, depending upon the particular implementation of the same, as readily understood by one of ordinary skill in the art. For example, various types of wireless and/or wired input and/or output devices can be used. Moreover, additional processors, controllers, memories, and so forth, in various configurations can also be utilized as readily appreciated by one of ordinary skill in the art. These and other variations of the processing system 500 are readily contemplated by one of ordinary skill in the art given the teachings of the present disclosure provided herein.

It is to be understood that although this disclosure includes a detailed description on cloud computing, implementation of the teachings recited herein are not limited to a cloud computing environment. Rather, embodiments of the present disclosure are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service.

A cloud computing environment is service oriented with a focus on statelessness, low coupling, modularity, and semantic interoperability. At the heart of cloud computing is an infrastructure that includes a network of interconnected nodes.

Figure 6:
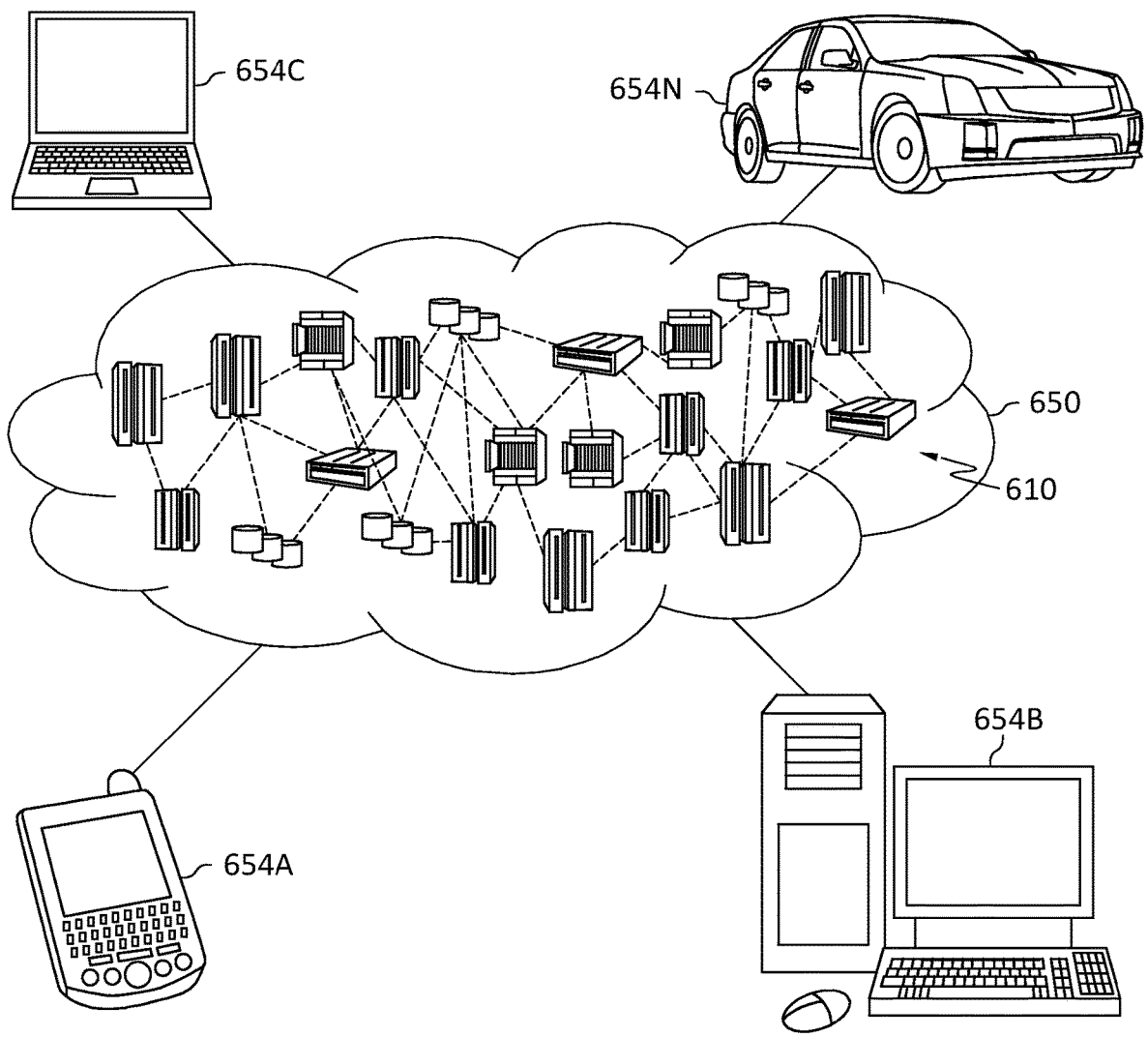
FIG. 6 is a block diagram of an illustrative cloud computing environment having one or more computing nodes with which local computing devices used by cloud customers to communicate, according to embodiments.

Referring now to FIG. 6, illustrative cloud computing environment 650 is depicted. As shown, cloud computing environment 650 includes one or more cloud computing nodes 610 with which local computing devices used by cloud consumers, such as, for example, personal digital assistant (PDA) or cellular telephone 654A, desktop computer 654B, laptop computer 654C, and/or automobile computer system 654N may communicate. Nodes 610 may communicate with one another. They may be grouped (not shown) physically or virtually, in one or more networks, such as Private, Community, Public, or Hybrid clouds as described hereinabove, or a combination thereof. This allows cloud computing environment 650 to offer infrastructure, platforms and/or software as services for which a cloud consumer does not need to maintain resources on a local computing device. It is understood that the types of computing devices 654A-N shown in FIG. 6 are intended to be illustrative only and that computing nodes 610 and cloud computing environment 650 can communicate with any type of computerized device over any type of network and/or network addressable connection (e.g., using a web browser).

Figure 7:
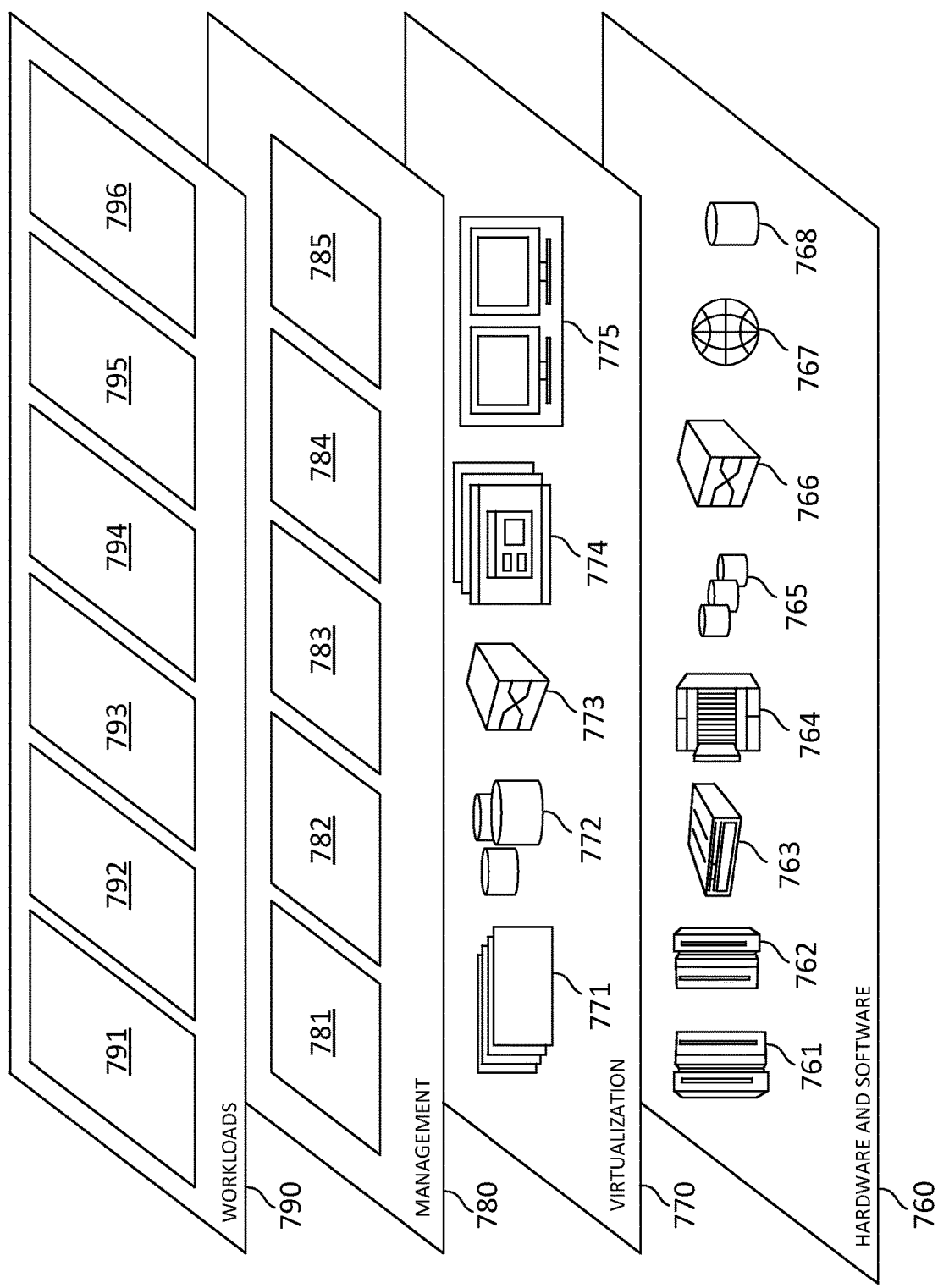
FIG. 7 is a block diagram of a set of functional abstraction layers provided by a cloud computing environment, according to embodiments.

Referring now to FIG. 7, a set of functional abstraction layers provided by cloud computing environment 650 (FIG. 6) is shown. It should be understood in advance that the components, layers, and functions shown in FIG. 7 are intended to be illustrative only and embodiments of the invention are not limited thereto. As depicted, the following layers and corresponding functions are provided:

Hardware and software layer 760 includes hardware and software components. Examples of hardware components include: mainframes 761; RISC (Reduced Instruction Set Computer) architecture-based servers 762; servers 763; blade servers 764; storage devices 765; and networks and networking components 766. In some embodiments, software components include network application server software 767 and database software 768.

Virtualization layer 770 provides an abstraction layer from which the following examples of virtual entities may be provided: virtual servers 771; virtual storage 772; virtual networks 773, including virtual private networks; virtual applications and operating systems 774; and virtual clients 775.

In one example, management layer 780 may provide the functions described below. Resource provisioning 781 provides dynamic procurement of computing resources and other resources that are utilized to perform tasks within the cloud computing environment. Metering and Pricing 782 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 783 provides access to the cloud computing environment for consumers and system administrators. Service level management 784 provides cloud computing resource allocation and management such that required service levels are met. Service Level Agreement (SLA) planning and fulfillment 785 provide pre-arrangement for, and procurement of, cloud computing resources for which a future requirement is anticipated in accordance with an SLA.

Workloads layer 790 provides examples of functionality for which the cloud computing environment may be utilized. Examples of workloads and functions which may be provided from this layer include: mapping and navigation 791; software development and lifecycle management 792; virtual classroom education delivery 793; data analytics processing 794; transaction processing 795; and bioprinted tongue knowledge corpus training processing 796.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions.

The descriptions of the various embodiments have been presented for purposes of illustration and are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. An artificial tongue comprising:
   tongue tissue formed by a bioprinting process;
   an antenna embedded within the tongue tissue and configured to wirelessly receive power from an external device;
   a processor embedded within the tongue tissue and operatively coupled to the antenna; and
   a piezoelectric element embedded within the tongue tissue and operatively coupled to the processor, the piezoelectric element configured to deform in response to an applied electric bias,
   wherein the processor is configured to cause the electric bias to be applied to the piezoelectric element based on the power received by the antenna.

2. The artificial tongue of claim 1, wherein a plurality of the piezoelectric elements are embedded at different locations and/or orientations within the tongue tissue, wherein the processor is configured to individually cause different electrical biases to be applied to at least some of the plurality of piezoelectric elements thereby causing different portions of the tongue tissue to deform.

3. The artificial tongue of claim 2, wherein the plurality of piezoelectric elements are configured to, upon selective deformation, cause the tongue tissue to change position within an oral cavity of a user, the changed position of the tongue tissue corresponding to a type of sound.

4. The artificial tongue of claim 1, wherein the piezoelectric element is a stripe actuator comprising two elongated stripe-shaped ceramic layers electrically connected in parallel.

5. The artificial tongue of claim 1, wherein the antenna is further configured to receive instructions from the external device that, when processed by the processor, cause the electric bias to be applied to the piezoelectric element.

6. The artificial tongue of claim 5, wherein the instructions are based on a knowledge corpus generated by a deep learning neural network.

7. The artificial tongue of claim 6, wherein the knowledge corpus is generated by at least one of historical movement data of the tongue tissue, and MRI image analysis of the tongue tissue.

8. The artificial tongue of claim 1, wherein the external device includes a display element configured to display speech therapy instructions to a user.

9. The artificial tongue of claim 8, wherein the external device is configured to transmit speech therapy data to the processor through the antenna, the speech therapy data corresponding to the displayed speech therapy instructions.

10. The artificial tongue of claim 9, wherein the speech therapy data includes instructions that, when processed by the processor, cause the piezoelectric element to deform in a time-parallel manner with the speech therapy instructions that are displayed on the display element.

11. A method of manufacturing an artificial tongue, the method comprising:
bioprinting tongue tissue;
forming an antenna within the tongue tissue, the antenna configured to wirelessly receive power from an external device;
forming a processor within the tongue tissue, the processor being operatively coupled to the antenna; and
forming a piezoelectric element within the tongue tissue, the piezoelectric element being operatively coupled to the processor and configured to deform in response to an applied electric bias,
wherein the processor is configured to cause the electric bias to be applied to the piezoelectric element based on the power received by the antenna.

12. The method of claim 11, wherein a plurality of the piezoelectric elements are embedded at different locations and/or orientations within the tongue tissue, and wherein the processor is configured to individually cause different electrical biases to be applied to at least some of the plurality of piezoelectric elements thereby causing different portions of the tongue tissue to deform.

13. The method of claim 12, wherein the plurality of piezoelectric elements are configured to, upon selective deformation, cause the tongue tissue to change position within an oral cavity of a user, the changed position of the tongue tissue corresponding to a type of sound.

14. The method of claim 11, wherein forming the piezoelectric element includes forming two elongated stripe shaped ceramic layers, and electrically connecting the striped shaped ceramic layers in parallel.

15. The method of claim 11, wherein the antenna is further configured to receive instructions from the external device that, when processed by the processor, cause the electric bias to be applied to the piezoelectric element.

16. The method of claim 15, wherein the instructions are based on a knowledge corpus generated by a deep learning neural network.

17. The method of claim 16, wherein the knowledge corpus is generated by at least one of historical movement data of the tongue tissue, and MRI image analysis of the tongue tissue.

18. The method of claim 11, wherein the antenna is formed using a three-dimensional printing process.

19. The method of claim 11, wherein the processor is formed using a three-dimensional printing process.

20. The method of claim 11, wherein the piezoelectric element is formed using a three-dimensional printing process.

\* \* \* \* \*